United States Patent [19]

Garcia et al.

[11] Patent Number: 5,103,676
[45] Date of Patent: * Apr. 14, 1992

[54] METHOD OF NONCONTACTING ULTRASONIC PROCESS MONITORING

[75] Inventors: Gabriel V. Garcia, Las Cruces, N. Mex.; John B. Walter, Ammon; Kenneth L. Telschow, Idaho Falls, both of Id.

[73] Assignee: The United States of America as represented by the United States Department of Energy, Washington, D.C.

[*] Notice: The portion of the term of this patent subsequent to Mar. 19, 2008 has been disclaimed.

[21] Appl. No.: 642,578

[22] Filed: Jan. 17, 1991

Related U.S. Application Data

[63] Continuation-in-part of Ser. No. 478,375, Feb. 12, 1990, Pat. No. 5,000,046.

[51] Int. Cl.⁵ ............................................. G01N 29/02
[52] U.S. Cl. ...................................................... 73/597
[58] Field of Search ................. 73/597, 33 A, 643, 657

[56] References Cited

U.S. PATENT DOCUMENTS 4,773,267  9/1988  Abts ........................................ 73/597
5,000,046  3/1991  Garcia et al. ......................... 73/597

OTHER PUBLICATIONS

E. P. Papadakis and B. W. Peterson, "Ultrasonic Velocity as a Predictor of Density in Sintered Powdered Metal Parts", Material Evaluation 37(5), pp. 76-80 (1979).

R. L. Parker, J. R. Manning, & N. C. Peterson, "Application of Pulse-Echo Ultrasonics to Locate the Solid/Liquid Interface during Solidification and melting of Steel and Other Metals", Journal of Applied Physics, 58(11), Dec. 1985.

Primary Examiner—Hezron E. Williams
Assistant Examiner—Shu-Cheng Kau
Attorney, Agent, or Firm—Tyrone Davis; Robert J. Fisher; William R. Moser

[57] ABSTRACT

A method of monitoring a material during processing comprising the steps of (a) shining a detection light on the surface of a material; (b) generating ultrasonic waves at the surface of the material to cause a change in frequency of the detection light; (c) detecting a change in the frequency of the detection light at the surface of the material; (d) detecting said ultrasonic waves at the surface point of detection of the material; (e) measuring a change in the time elapsed from generating the ultrasonic waves at the surface of the material and return to the surface point of detection of the material, to determine the transit time; and (f) comparing the transit time to predetermined values to determine properties such as, density and the elastic quality of the material.

6 Claims, 3 Drawing Sheets

METHOD OF NONCONTACTING ULTRASONIC PROCESS MONITORING

CONTRACTUAL ORIGIN OF THE INVENTION

The U.S. Government has rights in this invention pursuant to Contract No. DE-AC07-76ID01570 between the U.S. Department of Energy and EG&G Idaho, Inc.

This application is a continuation in part of Ser. No. 478,375 filed Feb. 12, 1990 and now U.S. Pat. No. 5,000,046.

BACKGROUND OF THE INVENTION

The present invention relates to a method of noncontacting monitoring the elastic properties of a material in either a solid or liquid state and more particularly to that of a metal or ceramic material as disclosed in allowed U.S. patent application Ser. No. 478,375, herein incorporated by reference. The invention as disclosed is directed to a method using noncontacting laser ultrasonic monitoring at the surface to determine the density or elastic qualities of a material.

Consolidating ceramic components from powder compacts requires sintering at high temperatures during processing. Often, their mechanical properties are controlled by the residual porosity in the host material. Improvements in efficiency of production and in the properties of ceramics could be achieved if the porosity could be monitored during the processing stage. Feedback of this knowledge would allow the sintering process to be optimized and the porosity of the material to be controlled.

Several types of optical laser-base ultrasonic detectors have been developed for noncontacting measurement of surface motion due to ultrasonic waves. In some cases these devices have been employed at high temperatures to record material properties during heating. However, the majority of these systems depend on phase sensitive detection of the light and require polished surfaces and strict alignment for adequate signal-to-noise ratio, and thus are not suitable for processes, such as, sintering, and plasma and electron beam hearth melting.

Due to its noncontacting nature, laser-ultrasonic techniques now open the possibility for real-time monitoring of materials in very hostile environments, as is encountered during processing. Prior to this work, ultrasonic wave measurements of the sintering of ceramics used buffer rods which made direct contact with the material. Only optical access to the sample being sintered is required with the laser-ultrasonic method as described.

SUMMARY OF THE INVENTION

The present invention relates to a method of monitoring a material during processing and more particularly metals, ceramics and their composites. The technique is a synthesis of laser generation and laser detection for ultrasonic waves in solid materials, which can determine various elastic, acoustic and ultrasonic properties of materials in real-time and in a noncontacting manner for the purpose of process monitoring. It is accomplished by generating an ultrasonic wave echo at the surface of the material. A laser or equivalent may be used to generate an ultrasonic wave echo that travels through the material to the bottom surface and is reflected back to the top surface of the material, or along its top surface. Simultaneously, a light preferably a laser is shined on the surface of the material and as the ultrasonic waves return to the surface of the material it causes a displacement at the surface of the pool. This displacement causes a change in the frequency of the light being shined on the surface of the material allowing for the returning ultrasonic waves to be detected by a detection device preferably an interferometer. Using a predetermined chart listing characteristics of the material such as, density, specific gravity, porosity, and other elastic qualities of the material, the recorded transit time of the ultrasonic wave to reflect off the bottom of the material or return to the point of detection can be used to monitor the progression and determine the density and elastic qualities of the material during processing.

It is therefore an object of this novel method to provide a noncontacting means to accurately monitor the density and elastic qualities of a material during processing and further another object of this novel method is to provide a means to monitor a molten material without causing a source of melt contamination.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects and in accordance with the purpose of the present invention, as embodied and broadly described herein, the novel method of monitoring a material, or a molten liquid pool process may comprise the steps of a). generating ultrasonic waves at the surface of the material; b). shining a detection light on a surface point of detection; c) detecting the change in frequency of the detection light; d). detecting the ultrasonic waves as they return to the surface point of detection; e). measuring the change in time elapsed for the ultrasonic waves to travel through the material and return to the surface point of detection to determine the transit time of the material; and comparing the transit time to a predetermined table to determine the density and elastic qualities of the material.

BRIEF DESCRIPTION OF THE DRAWINGS

The accompanying drawings, which are incorporated in and form part of the specification, illustrate an embodiment of the present invention and together with the description, serve to explain the principles of the invention. In the drawings.

DETAILED DESCRIPTION OF THE INVENTION

Figure 1:
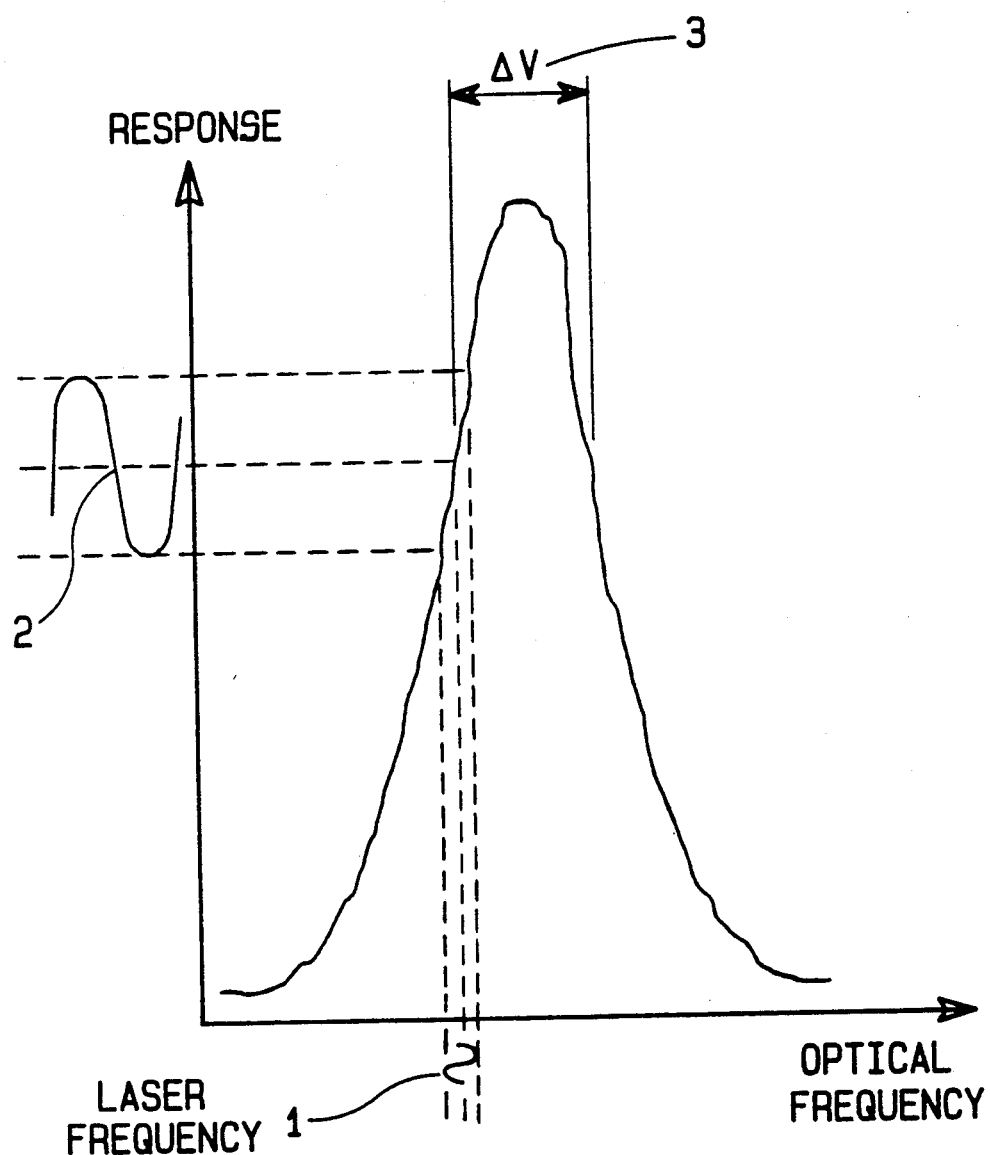
FIG. 1 is the frequency response graphic of the Fabry-Perot Interferometer.
Figure 2:
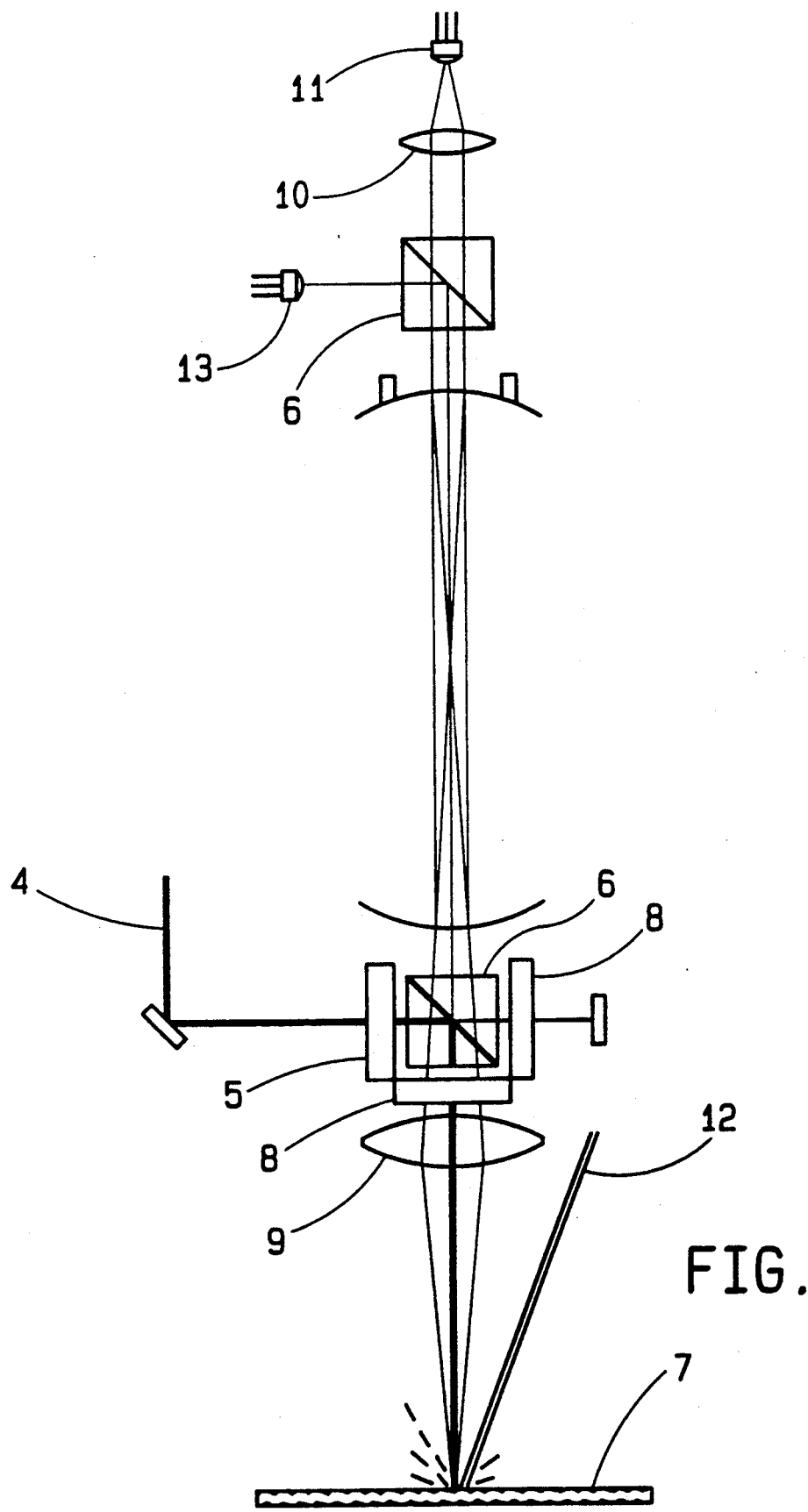
FIG. 2 shows an embodiment of a detection system using a pulsed laser to produce an ultrasonic wave echos.

Referring to FIGS. 1 and 2, in FIG. 1 a Fabry-Perot interferometer frequency response is shown. The oscillating material surface causes the reflected or scattered light to be Doppler shifted in frequency as indicated at 1. This light can be demodulated by passing it through an interferometer. Demodulation is accomplished by setting the interferometer along the slope of its response peak shown at position 2, thus giving an output intensity proportional to the Doppler frequency shift of the scattered or reflected light, and hence proportional to the change in velocity of the material surface. The bandwidth of the interferometer is shown at 3.

A ND:YAG Pulsed laser 12 is used to generate the ultrasonic waves at the material surface 7. The waves propagate to the bottom of the molten material and reflect off to return to the surface of the material. Upon returning to the surface the ultrasonic waves cause a motion of the material at the surface. A detection beam is generated by a 1-W argon ion laser beam 4 and is divided into two beams using a ½ wave plate 5 and a polarizing beam splitter cube 6. Part of the light goes to the material surface 7 for the detection of an ultrasonic wave while the rest is directed to a reference photodiode 13 to position the interferometer frequency response so that the laser frequency is at the operating point 2, near the half maximum of the curve. This has been found to provide the highest sensitivity for detecting a change in frequency of light with the Fabry-Perot interferometer. The two beams are kept separate using the beam splitter cubes 6 and ¼ wave plates 8. A collection lens 9 is used to capture scattered light off the molten surface 7. The light then travels through the interferometer where it is demodulated and through a lens 10 that focuses the light onto a signal photodiode 11 used to detect the ultrasonic waves. In operation, once the returning waves are detected, by the frequency shift in the detection beam directed at the surface of the material 7, the transit time for the material at that processing temperature is used to determine the density of the material. For example when processing ceramics, as the material becomes less porous during sintering, then the transit time for the ultrasonic waves to return to the surface point of detection should decrease as the velocity of sound increases for that material. Allowing the density or elastic qualities for that material to be calculated or projected for a particular fabrication process.

Figure 3:
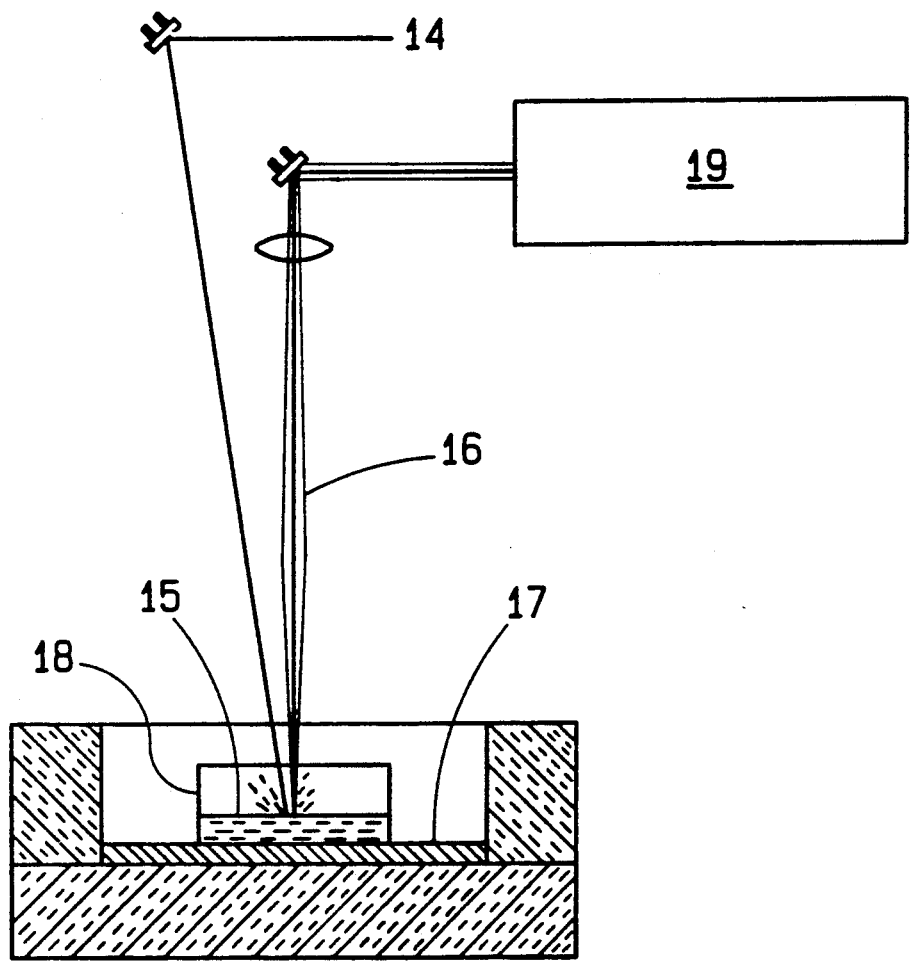
FIG. 3 shows another embodiment of apparatus arranged to effectuate the method.

FIG. 3, shows another arrangement of apparatus for affecting the invention which uses a ND:YAG pulsed laser 14 to produce longitudinal wave echos that travel through the molten material to the bottom surface and back to the top surface. A Fabry-Perot interferometer 19 detects the longitudinal wave echos at the surface of the molten material 15 by using an argon laser 16 as a light source. A tubular furnace 17 coupled with a temperature controller is used in sintering the material.

The foregoing description of the preferred embodiment of the invention has been presented for purposes of illustration and description. It is not intended to be exhaustive or to limit the invention to the precise form disclosed, and obviously many modifications and variations are possible in light of the above teaching.

The embodiments of the invention in which an exclusive property or privilege is claimed are defined as follows:

1. A noncontacting method of monitoring a molten liquid pool during processing comprising the steps of:
    (a) shining a detection light on a surface point of detection of said molten liquid pool;
    (b) generating ultrasonic waves at the surface of said molten liquid pool with a generating light to cause a change in frequency of said detection light;
    (c) detecting a change in the frequency of said detection light at the surface of said molten liquid pool;
    (d) detecting said ultrasonic waves at the surface point of detection of said molten liquid pool;
    (e) measuring a change in the elapsed from generating said ultrasonic waves surface of said molten liquid pool and in detecting said ultrasonic wave after they return to the surface of detection of said molten liquid pool, to a transit time for said molten liquid pool; and
    (f) comparing said transit time to predetermined values to determine the properties of said molten liquid pool.

2. A noncontacting method of monitoring a molten liquid pool during processing, as recited in claim 1, wherein:
    said step of detecting said ultrasonic waves after they return to the surface point of detection of said molten liquid pool, further comprises allowing said ultrasonic waves to cause motion at the surface of said molten liquid pool, thereby causing said detection light to change frequency at the surface of said molten liquid pool.

3. A noncontacting method of monitoring a molten liquid pool during processing, as recited in claim 2 wherein:
    said step of detecting the frequency change of said detection light is accomplished by using an interferometer.

4. A noncontacting method of monitoring a material during processing comprising the steps of:
    (a) shining a detection light on a surface point of detection of a material;
    (b) generating ultrasonic wave echos at the surface of said material with a generating light to cause a change in frequency of said detection light;
    (c) detecting a change in the frequency of said detection light at the surface of said material;
    (d) detecting said ultrasonic wave echos at the surface point of detection of said material;
    (e) measuring a change in the time elapsed from generating said ultrasonic wave echos at the surface of said material and in detecting said ultrasonic wave echos after they return to the surface point of detection of said material, to determine a transit time for said material; and
    (f) comparing said transit time to predetermined values to determine the elastic properties of said material.

5. A noncontacting method of monitoring a material during processing, as recited in claim 4, wherein:
    said step of detecting said ultrasonic wave echos after they return to the surface point of detection of said material, further comprises allowing said ultrasonic wave echos to cause motion at the surface of said material, thereby causing said detection light to change frequency at the surface of said material.

6. A noncontacting method of monitoring a material during processing, as recited in claim 5 wherein:
    said step of detecting the frequency change of said detection light is accomplished by using an interferometer.

* * * * *